United States Patent
Handa et al.

(10) Patent No.: US 9,611,465 B2
(45) Date of Patent: Apr. 4, 2017

(54) PHARMACEUTICAL COMPOSITION CONTAINING CORE FACTOR INVOLVED IN PROLIFERATION AND DIFFERENTIATION OF CENTRAL NERVOUS CELL

(71) Applicant: Celgene Corporation, Summit, NJ (US)

(72) Inventors: Hiroshi Handa, Tokyo (JP); Hideki Ando, Tokyo (JP); Takumi Itoh, Kanagawa (JP); Kentaro Hotta, Tokyo (JP)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 14/629,452

(22) Filed: Feb. 23, 2015

(65) Prior Publication Data

US 2015/0232826 A1   Aug. 20, 2015

Related U.S. Application Data

(62) Division of application No. 13/322,195, filed as application No. PCT/JP2010/058722 on May 24, 2010, now abandoned.

(30) Foreign Application Priority Data

May 25, 2009   (JP) ................. 2009-124811

(51) Int. Cl.
| | |
|---|---|
| *A61K 35/12* | (2015.01) |
| *C12N 15/12* | (2006.01) |
| *C12N 9/00* | (2006.01) |
| *A61K 48/00* | (2006.01) |
| *C12N 9/48* | (2006.01) |
| *A61K 38/00* | (2006.01) |

(52) U.S. Cl.
CPC ............. *C12N 9/48* (2013.01); *C12N 9/93* (2013.01); *A61K 38/00* (2013.01); *C12Y 304/00* (2013.01); *C12Y 603/02019* (2013.01)

(58) Field of Classification Search
CPC . A61K 38/00; C12N 9/48; C12N 9/93; C12Y 304/00; C12Y 603/02019
USPC ...... 424/93.7, 94.63; 435/18, 183, 212, 325, 435/4, 6.11
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,683,195 A | 7/1987 | Mullis et al. | |
| 4,810,643 A | 3/1989 | Souza | |
| 4,994,443 A | 2/1991 | Folkman et al. | |
| 4,999,291 A | 3/1991 | Souza | |
| 5,001,116 A | 3/1991 | Folkman et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,229,496 A | 7/1993 | Deeley et al. | |
| 5,354,556 A | 10/1994 | Sparks et al. | |
| 5,391,485 A | 2/1995 | Deeley et al. | |
| 5,393,870 A | 2/1995 | Deeley et al. | |
| 5,441,050 A | 8/1995 | Thurston et al. | |
| 5,573,758 A | 11/1996 | Adorante et al. | |
| 5,580,755 A | 12/1996 | Souza | |
| 5,582,823 A | 12/1996 | Souza | |
| 5,591,767 A | 1/1997 | Mohr et al. | |
| 5,593,990 A | 1/1997 | D'Amato | |
| 5,629,327 A | 5/1997 | D'Amato | |
| 5,635,517 A | 6/1997 | Muller et al. | |
| 5,639,476 A | 6/1997 | Oshlack et al. | |
| 5,674,533 A | 10/1997 | Santus et al. | |
| 5,698,579 A | 12/1997 | Muller | |
| 5,712,291 A | 1/1998 | D'Amato | |
| 5,733,566 A | 3/1998 | Lewis | |

(Continued)

FOREIGN PATENT DOCUMENTS

| | | |
|---|---|---|
| EP | 2 436 387 A1 | 4/2012 |
| JP | 11-504330 A | 4/1999 |

(Continued)

OTHER PUBLICATIONS

Aizawa et al., "mRNA distribution of the thalidomide binding protein cereblon in adult mouse brain," Neurosci. Res., 69:343-347 (2011).
Akhurst, "Taking thalifomide out of rehab," Nature Med., 16(4):370-372 (2010).
Aklilu et al., "Depletion of normal B cells with rituximab as an adjunct to IL-2 therapy for renal cell carcinoma and melanoma," Annals Oncology, 15:1109-1114 (2004).
Ando et al., "Efficient transfection strategy for the spatiotemporal control of gene expression in zebrafish," Mar. Biotechnol. (NY), 8(3):295-303 (2006).
Androutsellis-Theotokis et al., (2009) "Targeting neural precursors in the adult brain rescues injured dopamine neurons," Proc. Natl. Acad. Sci. U.S.A., 106 (32): 13570-5.
Angerer et al., in Genetic Engineering: Principles and Methods, Setlow and Hollaender, Eds., Plenum Press, New York, vol. 7, pp. 43-65 (1985).

(Continued)

*Primary Examiner* — Janet Epps-Smith
(74) *Attorney, Agent, or Firm* — Jones Day

(57) ABSTRACT

With an aim to provide a novel factor inducing proliferation of neural stem cells and differentiation of these cells into nerve cells, a pharmaceutical composition comprising 1) CRBN, 2) a nucleic acid encoding CRBN, or 3) a stem cell or a neural progenitor cell in which CRBN is expressed, a method including administering the pharmaceutical composition to a non-human animal and inducing proliferation of neural stem cells or neural progenitor cells of the non-human animal and differentiation of these cells into nerve cells, and a method for screening for a therapeutic drug for a disease of cerebral cortex or a surgical injury of cerebral cortex, using CRBN, are provided.

3 Claims, 8 Drawing Sheets

(56) References Cited

U.S. PATENT DOCUMENTS

| | | |
|---|---|---|
| 5,798,368 A | 8/1998 | Muller et al. |
| 5,874,448 A | 2/1999 | Muller et al. |
| 5,877,200 A | 3/1999 | Muller |
| 5,929,117 A | 7/1999 | Muller et al. |
| 5,955,476 A | 9/1999 | Muller et al. |
| 6,071,948 A | 6/2000 | D'Amato |
| 6,114,355 A | 9/2000 | D'Amato |
| 6,281,230 B1 | 8/2001 | Muller et al. |
| 6,316,471 B1 | 11/2001 | Muller et al. |
| 6,335,349 B1 | 1/2002 | Muller et al. |
| 6,380,239 B1 | 4/2002 | Muller et al. |
| 6,395,754 B1 | 5/2002 | Muller et al. |
| 6,403,613 B1 | 6/2002 | Man et al. |
| 6,458,810 B1 | 10/2002 | Muller et al. |
| 6,476,052 B1 | 11/2002 | Muller et al. |
| 6,555,554 B2 | 4/2003 | Muller et al. |
| 6,927,024 B2 | 8/2005 | Dodge et al. |
| 7,091,353 B2 | 8/2006 | Robarge et al. |
| 7,101,663 B2 | 9/2006 | Godfrey et al. |
| 7,122,799 B2 | 10/2006 | Hsieh et al. |
| 7,186,507 B2 | 3/2007 | Bacallao et al. |
| 7,244,759 B2 | 7/2007 | Muller et al. |
| 7,393,862 B2 | 7/2008 | Zeldis |
| 7,468,363 B2 | 12/2008 | Zeldis |
| 7,635,700 B2 | 12/2009 | Muller et al. |
| 8,143,283 B1 | 3/2012 | D'Amato |
| 9,217,743 B2 * | 12/2015 | Handa .......... G01N 33/566 |
| 2002/0045643 A1 | 4/2002 | Muller et al. |
| 2003/0045552 A1 | 3/2003 | Robarge et al. |
| 2003/0096841 A1 | 5/2003 | Robarge et al. |
| 2004/0029832 A1 | 2/2004 | Zeldis |
| 2004/0220144 A1 | 11/2004 | Zeldis |
| 2006/0134767 A1 | 6/2006 | Buser-Doepner et al. |
| 2006/0188475 A1 | 8/2006 | Xu et al. |
| 2006/0205787 A1 | 9/2006 | Muller et al. |
| 2007/0015194 A1 | 1/2007 | Shohat et al. |
| 2007/0049618 A1 | 3/2007 | Muller et al. |
| 2007/0065888 A1 | 3/2007 | Ring et al. |
| 2007/0128636 A1 | 6/2007 | Baker et al. |
| 2008/0051379 A1 | 2/2008 | Lerner et al. |
| 2008/0280779 A1 | 11/2008 | Shaughnessy et al. |
| 2009/0023149 A1 | 1/2009 | Knudsen |
| 2009/0142297 A1 | 6/2009 | Muller et al. |
| 2009/0148853 A1 | 6/2009 | Schafer et al. |
| 2010/0021437 A1 | 1/2010 | Isacson et al. |
| 2010/0190656 A1 | 7/2010 | Li et al. |
| 2010/0284915 A1 | 11/2010 | Dai et al. |
| 2011/0070218 A1 | 3/2011 | Teichberg et al. |
| 2011/0196150 A1 | 8/2011 | Man et al. |
| 2011/0200998 A1 | 8/2011 | Weichselbaum et al. |
| 2011/0223157 A1 | 9/2011 | Schafer et al. |
| 2012/0035347 A1 | 2/2012 | Yver |
| 2012/0077741 A1 | 3/2012 | Delfani et al. |
| 2012/0134969 A1 | 5/2012 | Handa et al. |
| 2012/0192297 A1 | 7/2012 | Handa et al. |
| 2012/0230983 A1 | 9/2012 | Muller et al. |
| 2012/0322073 A1 | 12/2012 | Lopez-Girona et al. |
| 2013/0177644 A1 | 7/2013 | Zeldis |
| 2013/0302323 A1 | 11/2013 | Zeldis |
| 2014/0045843 A1 | 2/2014 | Schafer et al. |
| 2014/0051591 A1 | 2/2014 | O'Donnell et al. |
| 2014/0066480 A1 | 3/2014 | Stewart et al. |
| 2014/0162282 A1 | 6/2014 | Schafer et al. |

FOREIGN PATENT DOCUMENTS

| | | |
|---|---|---|
| WO | WO 93/18186 A1 | 9/1993 |
| WO | WO 98/03502 A1 | 1/1998 |
| WO | WO 98/54170 A1 | 3/1998 |
| WO | WO 02/059106 A1 | 8/2002 |
| WO | WO 2007/108968 A2 | 9/2007 |
| WO | WO 2009/075797 A2 | 6/2009 |
| WO | WO 2011/049043 A1 | 4/2011 |
| WO | WO 2012/125405 A2 | 9/2012 |
| WO | WO 2012/125438 A1 | 9/2012 |
| WO | WO 2012/125459 A1 | 9/2012 |
| WO | WO 2012/125475 A1 | 9/2012 |
| WO | WO 2012/149299 A2 | 11/2012 |
| WO | WO 2012/153187 A2 | 11/2012 |
| WO | WO 2014/028445 A2 | 2/2014 |

OTHER PUBLICATIONS

Angers et al., "Molecular architecture and assembly of the DDB1-CUL4A ubiquitin ligase machinery," Nature, 443:590-5934 (2006).

Anolik et al., "B cell reconstitution after rituximab treatment of lymphoma recapitulates B cell ontogeny," Clin. Immunol., 122:139-145 (2007).

Ausubel et al. (eds.), Short Protocols in Molecular Biology, Fifth Edition, John Wiley and Sons, New York, Chapter 11 (2002).

Babin et al., "Zebrafish models of human motor neuron diseases: advantages and limitations," Prog. Neurobiol., 118:36-58 (2014).

Bartlett, "Regulation of neural stem cell differentiation in the forebrain," Immunol. Cell Biol., 76(5):414-418 (1998).

Basel-Vanagaite et al., "The CC2D1A, a member fo a new gene family with C2 domains, is involved in autosomal recessive non-syndromic mental retardation," J. Med. Genet., 43:203-210 (2006).

Basel-Vanagaite, "Genetics of autosomal recessive non-syndromic mental retardation: recent advances," Clin Genet. 72(3):167-74 (2007).

Basson, "Thalidomide's early effects," Nature Med., 16(4):372 (2010).

Bea et al., "Diffuse large B-cell lymphoma subgroups have distinct genetic profiles that influence tumor biology and improve gene-expression-based survival prediction," Blood, 106(9):3183-3190 (2005).

Becker et al. (2008) "Adult zebrafish as a model for successful central nervous system regeneration" Restorative Neurol. Neurosci. 26:71-80.

Bisht et al., "Brain drug delivery system: a comprehensive review on recent experimental and clinical findings," IJPSR, 2(4):792-806 (2011).

Bonnamain et al., (2012). "Neural stem/progenitor cells as promising candidates for regenerative therapy of the central nervous system," Frontiers in Cellular Neuroscience, 6: 17.

Boyd et al., "High expression levels of the mammalian target of rapamycin inhibitor DEPTOR are predictive of response to thalidomide in myeloma," Leukemia & Lymphoma, 51(11):2126-2129 (2010).

Bredesen et al., (2006) "Cell death in the nervous system," Nature, 443 (7113): 796-802.

Bruggermann et al., "Designer mice: the production of human antibody repertoires in transgenic animals," Year Immunol., 7:33-40 (1993).

Burchiel et al., Immunopharmacokinetics of Radiolabeled Antibodies and Their Fragments, Masson Publishing, Inc., Chapter 13 (1982).

Burington et al., "Tumor cell gene expression changes following short-term in vivo exposure to single agent chemotherapeutics are related to survival in multiple myeloma," Clin. Cancer Res., 14(15):4821-4829 (2008).

Bustin et al., "Real-time reverse transcription PCT (qRT-PCR) and its potential use in clinical diagnosis," Clin. Sci., 109:365-379 (2005).

Cairns et al., "Regulation of cancer cell metabolism," Nature Rev., 11:85-95 (2011).

Cancer: Principles & Practice of Oncology, Third Edition, J. B. Lippincott Co., Philadelphia, PA, pp. 1843-1847 (1989).

Carstensen, Drug Stability: Principles & Practices, Second Edition, Marcel Dekker, New York, NY, pp. 379-380 (1995).

Cerny et al., "Advances in the treatment of non-Hodgkin's lymphoma," Ann. Oncol., 13 Suppl., 4:211-216 (2002).

Chang et al., "What is the functional role of the thalidomide binding protein cereblon," Int. J. Biochem Mol. Biol., 2(3):287-294 (2011).

Charoenfuprasert et al., "Identification of salt-inducible kinase 3 as a novel tumor antigen associated with tumorigenesis of ovarian cancewr," Oncogene, 2011, 30: 3570-3584.

(56) References Cited

OTHER PUBLICATIONS

Chothia et al., "Structural determinants in the sequence of immunoglobulin variable domain," J. Mol. Biol., 278:457-479 (1998).
Chow et al., "In vivo drug-response in patients with leukemic non-Hodgkin's lymphomas is associated with in vitro chemosensitivity and gene expression profiling," Pharmacological Research, 2006, 53:49-61.
Christian et al., "p62 (SQSTM1) and cyclic AMP phospodiesterase-4A4 (PDE4A4) locate to a novel, reversible protein aggregate with links to autophagy and proteasome degradation pathways," Cellular Signaling, 22:1576-1596 (2010).
Clarke et al., "Changing incidence of non-Hodgkin lymphomas in the United States," Cancer, 94(7):2015-2023 (2002).
Corral et al., "Immunomodulation by thalidomide and thalidomide analogues," Ann. Rheum. Dis., 58:(Suppl I)I117-I113 (1999).
Cuoco et al., "Microarray based analysis of an inherited terminal 3p26.3 deletion, containing only the CHL1 gene, from a normal father to his two affected children," Orphanet J Rare Dis., 6:12 (2011).
Dufour-Rainfray et al., "Fetal exposure to teratogens: evidence of genes involved in autism," Neurosci Biobehav Rev., (2011).
Emens et al., "Chemotherapy: friend of foe to cancer vaccines," Curr. Opin. Mol. Ther., 3(1):77-84 (2001).
English translation of International Preliminary Report on Patentability issued in PCT/JP2010/058722 on Dec. 15, 2011.
Ferraiuolo et al., "Microarray analysis of the cellular pathways involved in the adaptation to and progression of motor neuron injury in the SOD1 G93A mouse model of familial ALS," J. Neurosci., 27(34):9201-9219 (2007).
Fleisch et al. (2011) "Investigating regeneration and functional integration of CNS neurons: Lessons from zebrafish genetics and other fish species" Biochem. Biophys. Acta 1812:364-380.
Flemming, "Target indentification: Unravelling thalidomide teratogenicity," Nature Rev. Drug Discov., 9:361 (2010).
Folkman et al., "Angiogenesis inhibition and tumor regression caused by heparin or a heparin fragment in the presence of cortisone," Science, 221:719-725 (1983).
Fukuchi, "Ligand-dependent degradation of Smad3 by a ubiquitin ligase complex of ROC1 and associated proteins," Molecular Biology of The Cell, 12(5): 1059-1524 (2001).
Gall et al., "Nucleic acid hybridization in cytological preparations," Methods Enzymol., 21:470-480 (1981).
Galustian et al., "Lenalidomide: a novel anticancer drug with multiple modalities," Expert Opin. Pharmacother., 10(1):125-133 (2009).
Garshasbi et al., "A defect in the TUSC3 gene is associated with autosomal recessive mental retardation," Am. J. Hum. Genetics, 82:1158-1164 (2008).
Garshasbi et al., "Two independent mutations in the ZC3H14 gene are associated with non-syndromic autosomal recessive mental retardation," Medizinische Genetik, 22(1): 83 (2010).
Genbank Accession No. NP_001166953; GI No. 291045198 (Nov. 24, 2013).
Genbank Accession No. NP_057386; GI No. 39545580 (Sep. 23, 2013).
Gladman et al., Kelley's Textbook of Rheumatology, 2 Vols. 6th Edition, W. B. Saunders Company, Chapter 71, pp. 1071-1073 (2001).
Gladman, "Current concepts in psoriatic arthritis," Curr. Opin. Rheumatol., 14(4):361-366 (2002).
Gupta D et al., "Adherence of Multiple Myeloma Cells to Bone Marrow Stromal Cells Up Regulates Vascular Endothelial Growth Factor Secretion: Therapeutic Applications," Leukemia, 2001, 15 (12): 1950-1961.
Heintel et al., "High Expression of the thalidomide-binding protein cereblon (CRBN) is associated with improved clinical response in patients with multiple myeloma treated with lenalidomide and dexamethasone," 53rd ASH Annual Meeting and Exposition, Abstract 2879 (Dec. 10-13, 2011).
Hernandez et al., "Thalidomide modulates mycobacterium lepraeinduced NF-κB pathway and lower cytokine response," Eur. J. Pharmacol., 670:272-279 (2011).
Higgins et al., "A mutation in a novel ATP-dependent Lon protease gene in a kindred with mild mental retardation," Nuerology, 63(10):1927-1931 (2004).
Higgins et al., "Candidate genes for recessive non-syndromic mentalretardation on chromosome 3p (MRT2A)," Clin. Genet., 65:496-500 (2004).
Higgins et al., "Dysregulation of large-conductance Ca2+-activated K+ channel expression in nonsyndromal mental retardation due to a cereblon p.R419X mutation," Neurogenetics, 9:219-223 (2008).
Higgins et al., "Temporal and spatial mouse brain expression of cereblon, an ionic channel regulator involved in human intelligence," J. Neurogenetics, 24:18-26 (2010).
Hohberger et al., "Cereblon is expressed in the retina and binds to voltage-gated chloride channels," FEBS Lett., 583:633-637 92009).
Hsich et al., "Review: Critical issues in gene therapy for neurologic disease," Human Gene Ther., 13:579-604 (1998).
International Search Report for PCT/US2013/048510 mailed Apr. 4, 2014.
Ito et al., "CRBN, a mental retardation-related protein, forms a novel E3 ubiquitin ligase complex with DDB1," Dai 80 Kai The Japanese Society Taikai, Dai 30 Kai The Molecular Biology Society of Japan Nenkai Godo Taikai Koen Yoshishu, pp. 4P-1011 (2007).
Ito et al., "Deciphering the mystery of thalidomide teratogenicity," Congenital Anomalies, 52:1-7 (2012).
Ito et al., "Identification of a primary target of thalidomide teratogenicity," Science, 327:1-28 (2010).
Ito et al., "Identification of a primary target of thalidomide teratogenicity," Science, 327(5971):1345-1350 (2010).
Ito et al., "Teratogenic effects of thalidomide: molecular mechanisms," Cell. Mol. Life Sci., 68(9):1569-1579 (2011).
Jakobovits et al., "Analysis of homozygous mutant chimeric mice: deletion of the immunoglobulin heavy-chain joining region blocks B-cell development and antibody production," Proc. Natl. Acad. Sci., USA, 90:2551-2555 (1993).
Jakobovits et al., "Germ-line transmission and expression of human-derived yeast artificial chromosome," Nature, 362(6417):255-258 (1993).
Jakobsson et al., "Lentiviral vectors for use in the central nervous system," Mol. Ther., 13(3):484-493 (2006).
Jalkanen et al., "Cell surface proteoglycan of mouse mammary epithelial cells is shed by cleavage of its matrix-binding ectodomain from its membrane-associated domain," J. Cell Biol., 105(6 Pt 2):3087-3096 (1987).
Jalkanen et al., "Heparan sulfate proteoglycans from mouse mammary epithelial cells: localization on the cell surface with a monoclonal antibody," J. Cell Biol., 101(3):976-984 (1985).
Jemal et al., "Cancer Statistics," CA Cancer J. Clin., 57:43-66 (2007).
Jo et al., "Identification and functional characterization of cereblon as a binding protein for large-conductance calcium-activated potassium channel in rat brain," J. Neurochem., 94(5):1212-1224 (2005).
Johansson, (2007) "Regeneration and plasticity in the brain and spinal cord," J Cereb Blood Flow Metab, 27:1417-1430.
Jones et al., "Pharmaceutical cocrystals: an emerging approach to physical property enhancement," MRS Bulletin 31:875-879 (2006).
Kabat et al., "Attempts to locate complementarity-determining residues in the variable positions of light and heavy chains," Ann N.Y. Acad. Sci., 190:382-393 (1971).
Kallioniemi et al., "Comparative genomic hybridization for molecular cytogenetic analysis of solid tumors," Science 258:818-821 (1992).
Kamarch, "Fluorescence-activated cell sorting of hybrid and transfected cells," Methods Enzymol., 151:150-165 (1987).
Kantarci et al, "Identification of the genetic basis of nonsyndromic intellectual disability in large consanguineous families by exome sequencing," Clin. Genet., 78(Suppl. 1):L03 (2010).
Kim et al., "Thalidomide: the tragedy of birth defects and the effective treatment of disease," Toxicological Sci., 122(1):1-6 (2011).

(56) References Cited

OTHER PUBLICATIONS

Kim et al., "Use of absolute lymphocyte counts to predict response to chemotherapy and survival in diffuse large B-cell lymphoma," J. Clin. Oncology, ASCO Annual Meeting Proceedings Part I., 25(18S), Jun. 20 Supplement, p. 8082 (2007).
Kishimoto et al. (2012) "Neuronal regeneration in zebrafish model of adult brain injury" Disease Models and Mechanisms 5:200-209.
Knobloch et al., Apoptosis induction by thalidomide: critical for limb teratogenicity but therapeutic, Current Mol. Pharmacol., 4:26-61 (2011).
Kobayashi et al., "Overexpression of the forebrain-specific homeobox gene six3 induces rostral forebrain enlargement in zebrafish," Development, 125:2973-2982 (1998).
Kohler et al., "Continuous cultures of fused cells secreting antibody of predefined specificity," Nature, 256:495-497 (1975).
Kumar et al., "Occurrence of Multiple Myeloma in Both Donor and Recipient After Bone Marrow Transplantation." American Journal of Hematology, 2002, 71: 227-228.
Lee et al., "Cereblon binding modulates AMP-activated protein kinase function," Journal of Neurochemistry, 115(WE03-03): 74 (2010).
Lee et al., "Cereblon inhibits proteasome activity by binding to the 20S core proteasome subunit beta type 4," Biochem. Biophys. Res. Comm., 427:618-622 (2012).
Lee et al., "Embryopathic effects of thalidomide and its hydrolysis products in rabbit embryo culture: evidence for a prostaglandin H synthase (PHS)-dependent, reactive oxygen species (ROS)-mediated mechanism," FASEB J., 25:2468-2483 (2011).
Lee et al., "Functional modulation of AMP-activated protein kinase by cereblon," Biochimica Biophysica Acta, 1813:448-455 (2011).
Lee et al., "Induction of cereblon by NF-E2-related factor 2 in neuroblastoma cells exposed to hypoxia-reoxygenation," Biochem. Biophys. Res. Comm., 399:711-715 (2010).
Lee et al., "Resistance of CD-1 and ogg1 DNA repair-deficient mice to thalidomide and hydrolysis product embryopathies in embryo culture," Toxicological Sci., 122(1):146-156 (2011).
Lenz et al., "Molecular subtypes of diffuse large B-cell lymphoma arise by distinct genetic pathways," Proc. Natl. Acad. Sci., USA, 105(36):13520-13525 (2008).
Lenz et al., "Oncogenic CARD11 mutations in human diffuse large B cell lymphoma," Science, 319(5870):1676-1679 (2008).
List et al., "The myelodysplastic syndromes: biology and implications for management," J. Clin. Oncol., 8:1424-1441 (1990).
Lopez-Girona et al., "Direct Binding with Cereblon Mediates the Antiproliferative and Immunomodulatory Action of Lenalidomide and Pomalidomide," Blood, 2011, 118 (21): 335.
Lopez-Girona et al., "Cereblon is direct protein target for immunomodulatory and antiproliferative acttivities of lenalidomide and pomalidomide," Leukemia, 26:2326-2335 (2012).
Lopez-Girona et al., "Direct binding with cereblon mediates the antiproliferative and immunomodulatory action of lenalidomide and pomalidomide," 53rd ASH Annual Meeting and Exposition, 738, 22 pages (2011).
Lowe et al., "The PDE IV family of calcium-independent phosphodiesterase enzymes," Drugs of the Future, 17(9):799-807 (1992).
Lu et al., "MaxiK channel partners: Physiological Impact," Journal of Physiology, 570 (1): 65-72 (2006).
Ludwig et al., "IMWG consensus on maintenance therapy in multiple myeloma," Blood, 119(3): 3003-15 (2012).
Magavi et al., (2000), "Induction of neurogenesis in the neocortex of adult mice," Nature, 405 (6789): 951-5.
Mardis et al., "Recurring mutations found by sequencing an acute myeloid leukemia genome," N. Engl. J. Med., 361(11):1058-1066 (2009).
Marks et al., "By-passing immunization, human antibodies from V-gene libraries displayed on phage," J. Mol. Biol., 222(3):581-597 (1991).
Marriott et al., "Immunotherapeutic and antitumor potential of thalidomide analogues," Expert Opin. Biol. Ther., 1(4):1-8 (2001).

Martiniani et al., "Biological activity of lenalidomide and its underlying trherapeutic effects in multiple myeloma," Adv. Hematol., 2012:842945.
Michalak et al., "Testis-derived microRNA profiles of African clawed frogs (*Xenopus*) and their sterile hybrids," Genomics, 91(2): 158-64 (2008).
Mitchell et al., "Physical activity-associated gene expression signature in nonhuman primate motor cortex," Obesity, 20:692-698 (2012).
Mochida et al., "Genetic basis of developmental malformations of the cerebral cortex," Arch. Neurol., 61:637-640 (2004).
Muller et al., "Structural modifications of thalidomide produce analogs with enhanced tumor necrosis factor inhibitory activity," J. Med. Chem., 39(17):3238-3240 (1996).
Muller et al., "Thalidomide analogs and PDE4 inhibition," Bioorg. & Med. Chem. Lett., 8:2669-2674 (1998).
Mullis et al., "Specific enzymatic amplification of DNA in vitro: the polymerase chain reaction," Cold Spring Harbor Symp. Quant. Biol., 51:263-273 (1986).
Nakamura et al., "Freud-1/Akil, a novel PDK1-interacting protein, functions as a a scaffold to activate the PDK1/Akt pathway in epidermal growth factor signaling," Mol. Cell. Biol., 28(19):5996-6009 (2008).
Nakatomi et al., (2002) "Regeneration of Hippocampal Pyramidal Neurons after Ischemic Brain Injury by Recruitment of Endogenous Neural Progenitors," Cell, 110 (4): 429-41.
Neben et al., "High plasma basic fibroblast growth factor concentration is associated with response to thalidomide in progressive multiple myeloma," Clin. Cancer Res., 7(9):2675-2681 (2001).
Neve et al., "Gene delivery into the brain using viral vectors," Neuropsychopharmacology: The Fifth Generation of Progress, American College of Neuropsychopharmacology, Chapter 20 (2002).
Ngo et al., "Oncogenically active MYD88 mutations in human lymphoma," Nature, 470(7332)115-119 (2011).
Offidani et al., "Serum C-reactive protein at diagnosis and response to therapy is the most powerful factor predicting outcome of multiple myeloma treated with thalidomide/anthracycline-based therapy," Clin. Lymphoma & Myeloma, 8(5):294-299 (2008).
Parsons et al., "An integrated genomic analysis of human glioblastoma multiforme," Science, 321:1807-1812 (2008).
Paul (ed), Fundamental Immunology, Second Edition, Raven Press, New York, pp. 332-336 (1989).
Penichet et al., "Antibody-cytokine fusion proteins for the therapy of cancer," J. Immunol. Methods, 284:91-101 (2001).
Plückthun, The Pharmacology of Monoclonal Antibodies, vol. 113, Springer Verlag, Berlin, pp. 269-315 (1994).
Pohjola et al., "Terminal 3p deletions in two families—correlation between molecular karyotype and phenotype," American Journal of Medical Genetics, Part (2): 441-6 (2010).
Rajadhyaksha et al., "Behavioral characterization of cereblon forebrain-specific conditional null mice: a model for human non-syndromic intellectual disability," Behavioural Brain Res., 226:428-434 (2012).
Rajkumar, "Multiple myeloma: 2012 update on diagnosis, risk-stratification, and management," Am J Hematol., 87(1):78-88 (2012).
Rajpal et al., "A novel panel of protein biomarkers for predicting response to thalidomide-based therapy in newly diagnosed multiple myeloma patients," Proteomics, 11(8):1391-1402 (2011).
Razek et al., "Disorders of cortical formation: MR imaging features," AJNR Am. J. Neuroradiol., 30:4-11 (2009).
Rehmann et al., "The rise, fall and subsequent triumph of thalidomide: Lessons learned in drug development," Ther Adv Hematol., 2(5):291-308 (2011).
Ren et al., "Oncogenic CUL4A determines the response to thalidomide treatment in prostate cancer," J. Mol. Med., 90(10):1121-1132 (2012).
Ripa et al., "A linear model for the pharmacokinetics of azithromycin in healthy volunteers," Chemother., 42:402-409 (1996).
Roitt et al., Immunology, Third Edition, Mosby, St. Louis, MO, 17.1-17.12 (1993).

(56) References Cited

OTHER PUBLICATIONS

Santana et al., "Can zebrafish be used as animal model to study Alzheimer's disease," Am. J. Neurodegener. Dis., 1(1):32-48 (2012).
Schultheiss et al., "Pharmaceutical cocrystals and their physicochemcial properties," Cryst. Growth Des., 9(6):2950-2967 (2009).
Schütt et al., "Thalidomide in combination with dexamethasone for pretreated patients with multiple myeloma: serum level of soluble interleukin-2 receptor as a predictive factor for response rate and for survival," Ann. Hematol., 84(9):594-600 (2005).
Science Daily, "How many species on Earth? About 8.7 million, new estimate says," Retrieved online <http://www.sciencedaily.com/releases/2011/08/1108323180459.htm>, retrieved on Apr. 7, 2013.
Shackelford et al., "The LKB1-AMPK pathway: metabolism and growth control in tumour suppression," Nature Rev., 9:563-575 (2009).
Shan et al., "The role of cocrystals in pharmaceutical science," Drug Discov. Today, 13(9-10):440-446 (2008).
Shestopalov et al., "Oligonucleotide-based tools for studying zebrafish development," Zebrafish, 7(1):31-40 (2010).
Sokka et al., "MRI-guieded gas bubble enhanced ultrasound heating in in vivo rabbit thigh," Phys. Med. Biol., 48:223-241 (2003).
Stahnke et al., "Activation of apoptosis pathways in peripheral blood lymphocytes by in vivo chemotherapy," Blood, 98:3066-3073 (2001).
Staudt, "Gene expression profiling of lymphoid malignancies," Ann. Rev. Med., 53:303-318 (2002).
Suzuki et al., "Stabe transgene expression from HSV amplicon ectors in the brain: potential involvement of immunoregulatory signals," Mol. Ther., 16(10):1727-1736 (2008).
Takada et al., "Protective effect of thalidomide against N-methyl-D-aspartate-induced retinal neurotoxicity," J Neurosci Res., 89(10):1596-604 (2011).
Taylor et al., "A transgenic mouse that expresses a diversity of human sequence heavy and light chain immunoglobulins," Nucleic Acids Res., 20(23):6287-6295 (1992).
Taylor et al., "Protamine is an inhibitor of angiogenesis," Nature, 297:307-312 (1982).
The Merck Manual, 17th Edition, Merck & Company, West Point, PA, pp. 448, 944-952 (1999).
Therasse et al., "New guidelines to evaluate the response to treatment in solid tumors," J. Natl. Cancer Inst., 92(3):205-216 (2000).
Thomas et al., "Progess and problems with the use of viral vectors for gene," Nat. Rev. Genet., 4(5):346-358 (2003).
Thome et al., "Antigen receptor signaling to NF-κB via CARMA1, BCL10, and MALT1," Cold Spring Harb. Perspect. Biol., 2:a003004 (2010).
Tierney et al. (eds), Current Medical Diagnosis & Treatment 1998, 37th Edition, Appleton & Lange, Stamford, CT, p. 793 (1998).
Trask, "An overview of pharmaceutical cocrystals as intellectual property," Mol. Pharm., 4(3):301-309 (2007).
Vallet et al., "Update on immunomodulatory drugs (IMiDs) in hematologic and solid malignancies," Expert Opinion on Pharmacotherapy, vol. 13, No. 4 , pp. 473-494 (2012).
Vanhook, "Thalidomide Target Identified," Sci. Signal., vol. 3, Issue 113, p. ec82 (2010).
Vishweshwar et al., "Pharmaceutical co-crystals," J. Pharm. Sci., 95(3):499-516 (2006).
Wilen et al., "Strategies in optical resolutions," Tetrahedron, 33:2725-2736 (1977).
Wilen, Tables of Resolving Agents and Optical Resolutions, (E.L. Eliel, Ed.), University of Notre Dame Press, Notre Dame, IN, p. 268 (1972).
Willems, "Cognition genes on autosomes: The paradox," Clinical Genetics, 72(1): 9-12 (2007).
Wilson et al., "Novel disease targets and management approaches for diffuse large B-cell lymphoma," Leukemia & Lymphoma, 51(S1):1-10 (2010).
Wu et al., "Screening and indentification of host factors interacting with UL14 of herpes simplex virus 1," Med. Microbiol. Immunol., 200:203-208 (2011).
Wu, "Large-conductance Ca2+-activated K+ channels: physiological role and pharmacology," Current Medicinal Chemistry, 10(8):649-661 (2003).
Xin et al., "Primary function analysis of human mental retardation related gene CRBN," Mol. Biol. Rep., 35:251-256 (2008).
Yamazaki et al., "In vivo formation of a glutathione conjugate derived from thalidomide in humanized uPA-NOG mice," Chem Res Toxicol., 24(3):287-9 (2011).
Yang et al., "Exploiting synthetic lethality for the therapy of ABC diffuse large B cell lymphoma," Cancer Cell, 21:723-737 (2012).
Zhang et al., "PI3K/Akt signaling pathway is required for neuroprotection of thalidomide on hypoxic-ischemic cortical neurons in vitro," Brain Research, 1357: 157-65 (2010).
Zhu et al., "Molecular mechanism of action of immune-modulaotry drugs thalidomide, lenalidomide and pomalidomide in multiple myeloma," Leukemia & Lymphoma, 1-5 (2012).
Zhu et al., "Cereblon expression is required for the antimyeloma activity of lenalidomide and pomalidomide," Blood, 118(18):4771-4779 (2011).
Abnova, CRBN purified MaxPab mouse polyclonal antibody (B01P), Retrieved online <http://www.abnova.com/products/products_detail.asp?catalog_id=H00051185-B01P>, retrieved on Mar. 25, 2015.
Abrahams et al., "Methods used in the structure determination of bovine mitochondrial F1 ATPase," *Acta Crystallogr. D. Biol. Crystallogr.*, 52(Pt 1):30-42 (1996).
Adapt, Paterson Institute for Cancer Research, probests for CRBN, printed Dec. 2, 2013.
Aitipamula et al., "Polymorphs, salts, and cocrystals: what's in a name?," *Cryst. Growth Des.*, 12:2147-2152 (2012).
Altschul et al., "Gapped BLAST and PSI-BLAST: A new generation of protein database search programs," Nucleic Acid Res., 25(17):3389-3402 (1997).
Bedford et al., "Ubiquitin-like protein conjugation and the ubiquitin-proteasome system as drug targets," Drug Discovery, 10:29-46 (2011).
Bilal et al., "Generation of a 3D model for human cereblon using comparative modeling," J. Bioinformatics Sequence Analysis, 5(1):10-15 (2013).
Carter et al., *Chemotherapy of Cancer*, $2^{nd}$ edition, John Wiley & Sons, New York, NY, pp. 361-367 (1981).
Chamberlain et al., "Structure of the human Cereblon-DDB1-lenalidomide complex reveals basis for responsiveness to thalidomide analogs," Nature Struct. Mol. Biol., 21(9):803-809 (2014).
Chini et al., "The JAZ family of repressors is the missing link in jasmonate signalling," *Nature*, 448(7154):666-671 (2007).
De Graaff et al., "Matrix methods for solving protein substructures of chlorine and sulfur from anomalous data," *Acta Crystallogr. D. Biol. Crystallogr.*, 57(Pt 12):1857-1862 (2001).
Duman et al., "Crystal structures of bacillus subtilis lon protease," *J. Mol. Biol.*, 401(4):653-670 (2010).
Emsley et al., "Features and development of Coot," *Acta Crystallogr. D. Biol. Crystallogr.*, 66(Pt 4):486-501 (2010).
Eve et al., "Single-agent lenalidomide in relapsed/refractory mantle cell lymphoma: results from a UK phase II study suggest activity and possible gender differences," *Br. J. Haematol.*, 159(2):154-163 (2012).
Gandhi et al., "Measuring cereblon as a biomarker of response or resistance to lenalidomide and pomalidomide requires use of standardized reagents and understanding of gene complexity," *Br. J. Haematol.*, 164(2):233-244 (2013).
Gerdes et al., "Emerging understanding of multiscale tumor heterogeneity," *Front. Oncol.*, 4:1-12 (2014).
Gura, "Systems for identifying new drugs are often faulty," *Science*, 278:1041-1042 (1997).
He et al., "DDB1 functions as a linker to recruit receptor WD40 proteins to CUL4-ROC1 ubiquitin ligases," *Genes Dev.*, 20(21):2949-2954 (2006).
Hernandez-Ilizalitrurri et al., Higher Response to Lenalidomide in Relapsed/Refractory Diffuse Large B-Cell lymphoma in

(56) References Cited

OTHER PUBLICATIONS

Nongerminal Center B-Cell Like Than in Germinal Center B-Cell Like Phenotype, Cancer, pp. 5058-5066 (2011).
Higa et al., "CUL4-DDB1 ubiquitin ligase interacts with multiple WD40-repeat proteins and regulates histone methylation," *Nat. Cell. Biol.*, 8(11):1277-1283 (2006).
International Search Report for PCT/JP2010/058722 issued Jun. 22, 2010.
Kaiser, "First pass at cancer genome reveals complex landscape," *Science*, 313:1370 (2006).
Kim et al., "Gene Expression Profiles for the Prediction of Progression-free Survival in Diffuse Large B Cell Lymphoma: Results of a DASL Assay," Annals of Hematology, 93 (3): 437-447 (2013).
Krontiris et al., *Internal Medicine*, 4$^{th}$ edition, Elsevier Science, Chapters 71-72, pp. 699-729 (1994).
Li et al., "A promiscuous alpha-helical motif anchors viral hijackers and substrate receptors to the CUL4-DDB1 ubiquitin ligase machinery," *Nat. Struct. Mol. Biol.*, 17(1):105-111 (2010).
Li et al., "The RIG-I-like receptor LGP2 recognizes the termini of double-stranded RNA," *J. Biol. Chem.*, 284(20):13881-13891 (2009).
Lopez-Girona et al., "Lenalidomide downregulates the cell survival factor, interferon regulatory factor-4, providing a potential mechanistic link for predicting response," *Br. J. Haematol.*,154(3):325-336 (2011).
Lopez-Girona et al., "Direct binding with cereblon mediates the antiproliferative and immunomodulatory action of lenalidomide and pomalidomide," *53$^{rd}$ ASH Annual Meeting and Exposition*, Abstract 738 (Dec. 10-13, 2011).
Lu et al., "The structural basis of 5' triphosphate double-stranded RNA recognition by RIG-I C-terminal domain," *Structure*, 18(8):1032-1043 (2010).
McCoy et al., "Phaser crystallographic software," *J Appl. Crystallogr.*,40(Pt 4):658-674 (2007).
Ménard et al., Cereblon (CRBN) splicing could influence response to IMiDs : A new PCR strategy to easily detect and semi-quantify loss of the IMiDs binding domain, *Blood*, 122(21):3107 (2013).
Murshudov et al., "REFMAC5 for the refinement of macromolecular crystal structures," *Acta Crystallogr. D. Biol. Crystallogr.*, 67(Pt 4):355-367 (2011).
Newman et al., "Assessment of the effectiveness of animal developmental toxicity testing for human safety," Reprod. Toxicol., 7(4):359-390 (1993).
Oliver et al., "Immune stimulation in scleroderma patients treated with thalidomide," *Clin. Immunol.*, 97(2):109-120 (2000).
Otwinowski et al., "Processing of X-ray diffraction data collected in oscillation mode," *Methods Enzymol.*, 276:307-326 (1997).
Pannu et al., "Recent advances in the CRANK software suite for experimental phasing," *Acta Crystallogr. D.Biol. Crystallogr.*, 67(Pt 4):331-337 (2011).
Pannu et al., "The application of multivariate statistical techniques improves single-wavelength anomalous diffraction phasing," *Acta Crystallogr. D. Biol. Crystallogr.*, 60(Pt 1):22-27 (2004).
Parman et al., "Free radical-mediated oxidative DNA damage in the mechanism of thalidomide teratogenicity," *Nature Med.*, 5(5):582-585 (1999).
Patent Cooperation Treaty, International Search Report for application PCT/US2013/054663, mailed Aug. 21, 2014.
Petroski, "The ubiquitin system, disease, and drug discovery," *BMC Biochem.*, 9(Suppl. 1):S7 (2008).
Quach et al., "Mechanism of action of immunomodulatory drugs (IMiDS) in multiple myeloma," *Leukemia*, 24(1):22-32 (2010).
Ramsay et al., "Chronic lymphocytic leukemia cells induce defective LFA-1-directed T-cell motility by altering Rho GTPase signaling that is reversible with lenalidomide," *Blood*, 121(14):2704-2714 (2013).
Ramsay et al., "Multiple inhibitory ligands induce impaired T-cell immunologic synapse function in chronic lymphocytic leukemia that can be blocked with lenalidomide: establishing a reversible immune evasion mechanism in human cancer," *Blood*, 120(7):1412-1421 (2012).
Sheard et al., "Jasmonate perception by inositol-phosphate-potentiated COI1-JAZ co-receptor," *Nature*,468(7322):400-405 (2010).
Stockdale, *Medicine*, vol. 3, Rubenstein and Federman, eds., Chapter 12, Section IV and Section X (1998).
Tan et al., "Mechanism of auxin perception by the TIR1 ubiquitin ligase," *Nature*, 446(7136)640-645 (2007).
Thiel et al., "Small-molecule stabilization of protein-protein interactions: an underestimated concept in drug discovery?," *Angew Chem. Int. Ed. Engl.*, 51(9):2012-2018 (2012).
Vippagunta et al., "Crystalline solids," *Adv. Drug Del. Rev.*, 48:3-26 (2001).

\* cited by examiner

PHARMACEUTICAL COMPOSITION CONTAINING CORE FACTOR INVOLVED IN PROLIFERATION AND DIFFERENTIATION OF CENTRAL NERVOUS CELL

CROSS-REFERENCE TO RELATED APPLICATIONS

The present application is a divisional application of U.S. application Ser. No. 13/322,195 filed Nov. 23, 2011 (abandoned), which is a U.S. national stage application of International Application Serial No. PCT/JP2010/058722 filed May 24, 2010, which claims the benefit of priority to Japanese Application Serial No. 2009-124811 filed May 25, 2009, each of which is herein incorporated by reference in its entirety.

TECHNICAL FIELD

The present invention relates to a pharmaceutical composition used for treating a disease of cerebral cortex and the like, a method comprising administering the pharmaceutical composition to a non-human animal and inducing proliferation of neural stem cells or neural progenitor cells of the non-human animal and differentiation of these cells into nerve cells, and a method for screening for a therapeutic drug for a disease of cerebral cortex and the like.

BACKGROUND ART

The recent advancements in research on nerve cells have given rise to the possibility of regenerating brain that is lost by Alzheimer's disease, trauma, and the like. In such brain regeneration, elucidation of the factor inducing differentiation into nerve cells is important.

With regard to induction of differentiation into nerve cells, Mangale et al. have recently reported that a protein called Lhx2 induces neural stem cells or neural progenitor cells to become the cortex, while inhibiting induction of those cells to become the hippocampus (Mangale, V. S. et al., Science, Vol. 319, No. 5861, 304-309, 2008).

SUMMARY OF THE INVENTION

Technical Problem

As described above, if a factor that induces differentiation into nerve cells can be newly discovered, it would enable regenerating nerve cells, and using them for treating a disease of cerebral cortex such as Alzheimer's disease.

The present invention was completed under the foregoing technical background with an aim to provide a novel factor that induces differentiation into nerve cells.

Solution to Problem

The present inventors conducted intensive studies to solve the aforementioned problem. As a result, the present inventors have found that 1) a protein called CRBN (cereblon) functions to differentiate stem cells into neural stem cells or neural progenitor cells, and further into nerve cells, 2) CRBN induces proliferation of central nervous stem cells or neural progenitor cells, and 3) CRBN functions downstream of Lhx2, which is a known cerebral cortex selector factor.

CRBN is a protein that forms a ubiquitin ligase complex and its amino acid sequence is also publicly known; however, it has never been known before that CRBN functions to induce proliferation of central nervous stem cells or neural progenitor cells and differentiation of these cells into nerve cells.

There is a report by Higgins et al. describing the relationship between CRBN and the brain (J. J. Higgins et al., (2004), Neurology, 63, 1927-1931). Higgins et al. have reported that a family lineage involving mild mental retardation is observed to bear a mutated crbn gene. However, this report does not suggest that CRBN has the aforementioned functions.

The present invention was accomplished based on the foregoing findings.

That is, the present invention provides the following [1] to [11].

[1] A pharmaceutical composition comprising 1) CRBN, 2) a nucleic acid encoding CRBN, or 3) a stem cell or a neural progenitor cell in which CRBN is expressed.

[2] The pharmaceutical composition according to [1], wherein the nucleic acid encoding CRBN is inserted in a virus vector.

[3] The pharmaceutical composition according to [1], comprising CRBN and a protein that forms a ubiquitin ligase complex with CRBN.

[4] The pharmaceutical composition according to [1] or [2], comprising the nucleic acid encoding CRBN and a nucleic acid encoding a protein that forms a ubiquitin ligase complex with CRBN.

[5] The pharmaceutical composition according to [1], comprising a stem cell or a neural progenitor cell in which CRBN and a protein that forms a ubiquitin ligase complex with CRBN are expressed.

[6] The pharmaceutical composition according to any of [1] to [5], used for treating a disease of cerebral cortex or a surgical injury of cerebral cortex.

[7] The pharmaceutical composition according to any of [1] to [5], used for regenerating cerebral cortex.

[8] A method for comprising administering the pharmaceutical composition according to any of [1] to [7] to a non-human animal and proliferating a neural stem cell or a neural progenitor cell of the non-human animal.

[9] A method comprising administering the pharmaceutical composition according to any of [1] to [7] to a non-human animal and differentiating a neural stem cell or a neural progenitor cell of the non-human animal into a nerve cell.

[10] A method for screening for a therapeutic drug for a disease of cerebral cortex or a surgical injury of cerebral cortex, comprising contacting a test substance with a ubiquitin ligase complex containing CRBN and measuring a ubiquitin ligase activity of the ubiquitin ligase complex to select a test substance with an increased ubiquitin ligase activity.

[11] A method for screening for a therapeutic drug for a disease of cerebral cortex or a surgical injury of cerebral cortex, comprising culturing a neural stem cell or a neural progenitor cell in the presence of a test substance and measuring an expression level of CRBN in the neural stem cell or the neural progenitor cell to select a test substance with an increased expression level of CRBN.

Advantageous Effects of Invention

CRBN contained in the pharmaceutical composition of the present invention induces proliferation of central nervous stem cells or neural progenitor cells and differentiation of these cells into nerve cells. Accordingly, the pharmaceutical composition of the present invention is useful as a therapeutic drug for a disease of cerebral cortex such as Alzheimer's disease. Further, CRBN is also useful as a target substance for the development of a novel therapeutic drug for a disease of cerebral cortex.

INDUSTRIAL APPLICABILITY

The present invention is useful as a therapeutic drug for a disease of cerebral cortex such as Alzheimer's disease. Further, it is also useful for the development of a novel therapeutic drug for a disease of cerebral cortex.

DETAILED DESCRIPTION

Figure 1:
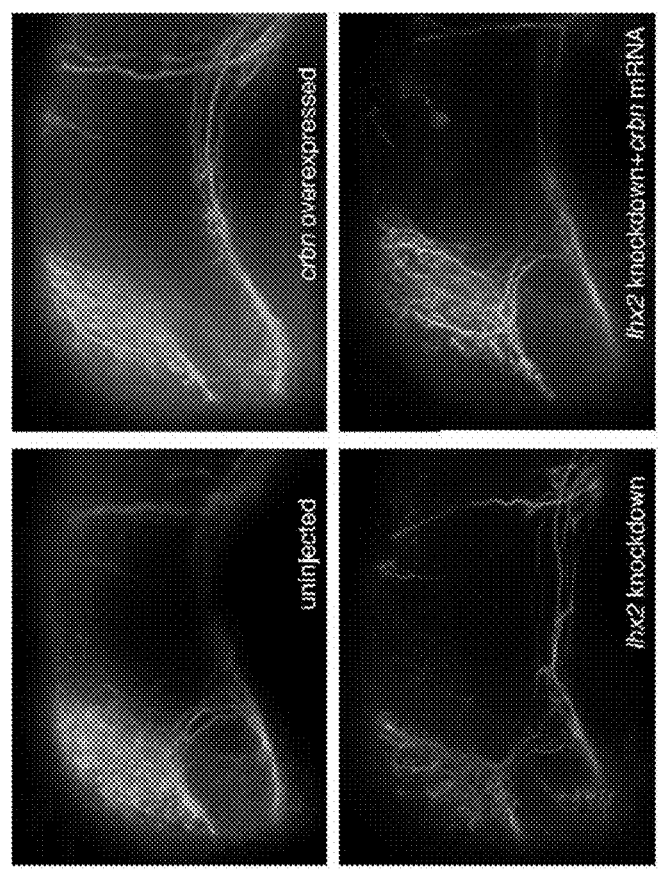
FIG. 1 shows fluorescence microscopic pictures of zebrafish embryos. In these pictures, the upper left shows a normal embryo, the upper right shows an embryo in which the crbn gene is overexpressed, the lower left shows an embryo in which the lhx2 gene is knocked down, and the lower right shows an embryo in which the lhx2 gene is knocked down while the crbn gene is overexpressed.

Hereinbelow, the present invention will be described in detail.

The pharmaceutical composition of the present invention comprises 1) CRBN, 2) a nucleic acid encoding CRBN, or 3) a stem cell or a neural progenitor cell in which CRBN is expressed.

CRBN is a known protein, and the base sequence of the gene encoding CRBN (crbn gene) is also published in a database. For example, the base sequences of human-derived crbn gene, mouse-derived crbn gene, rat-derived crbn gene, and zebrafish-derived crbn gene are registered in Entrez Gene under Gene ID: 51185, Gene ID: 58799, Gene ID: 297498, and Gene ID: 445491, respectively. Naturally-derived CRBN and crbn gene may be used, while modified CRBN capable of forming an active ubiquitin ligase complex, being composed of an amino acid sequence resulting from deletion, substitution, or addition of one or several amino acids in the amino acid sequence of naturally-derived CRBN and a gene encoding this modified form may be used.

The pharmaceutical composition of the present invention may contain any of CRBN, a nucleic acid encoding CRBN, and a stem cell or a neural progenitor cell in which CRBN is expressed as an active ingredient. The pharmaceutical composition containing these substances as an active ingredient can be prepared and used in a similar manner to a known drug containing a protein, a nucleic acid, a stem cell, and a progenitor cell as an active ingredient.

The nucleic acid encoding CRBN may be either DNA or RNA. The nucleic acid is preferably inserted in an appropriate vector so that it can act on neural stem cells in the brain. Examples of such a vector include a virus vector. Specific examples of the virus vector include an adenovirus vector, a retrovirus vector, and a lentivirus vector.

The stem cell in which CRBN is expressed is preferably an iPS cell derived from the patient him/her-self so as to be able to avoid rejection; however, other stem cells such as ES cells, adult stem cells, and cord blood stem cells may also be used. CRBN may be expressed in stem cells, and it is preferably overexpressed. A method for expressing or over-expressing CRBN can be carried out in accordance with, for example, the method of Ando et al. (Ando and Okamoto, Mar. Biotechnol. 8(3): 295-303, 2006), while it may also be carried out by other methods such as other microinjection methods, the caged RNA method (Ando et al., Nat. Genet. 28: 317-325, 2001), the electroporation method, the calcium phosphate method, the DEAE dextran method, the virus method, sonoporation method, and the transposon method.

No particular limitation is imposed on the administration method of the pharmaceutical composition of the present invention, and it can be appropriately determined according to the kind of the active ingredient, and the like. When CRBN or a nucleic acid encoding CRBN is used as active ingredients, the pharmaceutical composition can be administered by injection, drip infusion, and the like into the cerebral ventricle, the skin, the intraperitoneal cavity, the vein, the artery, or the spinal marrow fluid. Given that CRBN acts on the neural stem cells or neural progenitor cells in the brain, except for the case in which it is administered into the cerebral ventricle, it is preferable to provide such a treatment that would enable passage of CRBN through the blood brain barrier. As such a treatment, methods such as binding CRBN with essential endogenous substances that are actively taken up, carrying out structural modification of CRBN so as to avoid recognition by efflux transporters, and reducing the molecular weight to such a size that contains only a minimum functional domain may be possible. When stem cells or neural progenitor cells are used as active ingredients, the pharmaceutical composition is directly administered into the cerebral ventricle.

No particular limitation is imposed on the dose of the pharmaceutical composition of the present invention, and it can be appropriately determined according to the kind of the active ingredient, and the like. As for the daily dose for adults, when CRBN is administered, it is preferably administered in an amount of approximately 0.5 mg to 100 mg; when a nucleic acid encoding CRBN is administered, it is preferably administered in an amount of approximately 1 mg to 200 mg; and when a stem cell or a neural progenitor cell in which CRBN is expressed is administered, preferably 500 cells to 5000 cells are administered in a volume of approximately 50 μl to 500 μl.

When the pharmaceutical composition of the present invention is administered by injection or drip infusion, the injection fluid and the drip infusion fluid may contain components that are normally contained in these solutions. Examples of such a component include a liquid carrier (such as potassium phosphate buffer, physiological saline, Ringer's solution, distilled water, polyethylene glycol, plant oil and fat, ethanol, glycerin, dimethyl sulfoxide, and polypropylene glycol), antimicrobial agents, local anesthetics (such as procaine hydrochloride and dibucaine hydrochloride), buffer (such as tris-HCl buffer and hepes buffer), and osmotic pressure regulators (such as glucose, sorbitol, and sodium chloride).

The pharmaceutical composition of the present invention may contain: 1) in addition to CRBN, a protein that forms a ubiquitin ligase complex with CRBN, 2) in addition to a nucleic acid encoding CRBN, a nucleic acid encoding a protein that forms a ubiquitin ligase complex with CRBN, and 3) in addition to CRBN, a stem cell or a neural progenitor cell in which a protein that forms a ubiquitin ligase complex with CRBN are expressed. Examples of the protein that forms a ubiquitin ligase complex with CRBN include DDB1 (Damaged DNA Binding protein), Cul4A (Cullin 4A), Cul4B (Cullin 4B), and Roc1 (RBX1). Similarly to CRBN, these proteins are known proteins, and the base sequences of the genes encoding these proteins (i.e., ddb1 gene, cul4a gene, cul4b gene, and roc1 gene) are also published in a database. For example, the base sequences of human-derived ddb1 gene, mouse-derived ddb1 gene, rat-derived ddb1 gene, and zebrafish-derived ddb1 gene are registered in Entrez Gene under Gene ID: 1642, Gene ID: 13194, Gene ID: 64470, and Gene ID: 393599, respectively; the base sequences of human-derived cul4a gene, mouse-derived cul4a gene, rat-derived cul4a gene, and zebrafish-derived cul4a gene are registered in Entrez Gene under Gene ID: 8451, Gene ID: 99375, Gene ID: 361181, and Gene ID: 394002, respectively; the base sequences of human-derived cul4b gene, mouse-derived cul4b gene, rat-derived cul4b gene, and zebrafish-derived cul4b gene are registered in Entrez Gene under Gene ID: 8450, Gene ID: 72584, Gene ID: 302502, and Gene ID: 560313, respectively; and the base sequences of human-derived roc1 gene, mouse-derived roc1 gene, rat-derived roc1 gene, and zebrafish-derived roc1 gene are registered in Entrez Gene under Gene ID: 9978, Gene ID: 56438, Gene ID: 300084, and Gene ID: 449846, respectively. Each of these proteins and genes may be naturally-derived one, while a modified protein capable of forming an active ubiquitin ligase complex, being composed of an amino acid sequence resulting from deletion, substitution, or addition of one or several amino acids in the amino acid sequence of a naturally-derived protein and a gene encoding this modified protein may be used. The ubiquitin ligase complex contains, in addition to CRBN, three kinds of proteins, which are DDB1, CuL4A, and Roc1, or DDB1, CuL4B, and Roc1. Although the pharmaceutical composition of the present invention preferably contains (or expresses) all these three kinds of proteins (or nucleic acids encoding these proteins), it may contain only one or some of them.

The pharmaceutical composition of the present invention can be used for the treatment of a disease of cerebral cortex or a surgical injury of cerebral cortex, or for regenerating cerebral cortex. Examples of the disease of cerebral cortex include Alzheimer's disease, Parkinson's disease, Creutzfeldt-Jakob disease, Huntington's disease, progressive supranuclear palsy, and corticobasal degeneration.

Although the pharmaceutical composition of the present invention is intended to be used for humans, it may be administered to an animal other than humans to induce proliferation of the neural stem cells or neural progenitor cells or differentiation of these cells into nerve cells in these animals. The target animals are mainly vertebrates, and examples thereof include mice, rats, monkeys, dogs, ferrets, hamsters, chickens, xenopus, zebrafish, and medaka.

It has been confirmed only in zebrafish that CRBN induces proliferation of neural stem cells or neural progenitor cells and differentiation of these cells into nerve cells, as described in Examples. However, 70 to 80% of the genome synteny is conserved between humans and zebrafish (Nature Reviews Genetics 8, 353-367 (May 2007)). Accordingly, it is predicted that CRBN exhibits similar effects as those confirmed in zebrafish also in other vertebrates including humans.

Because CRBN induces proliferation of neural stem cells or neural progenitor cells and differentiation of these cells into nerve cells, the protein can be used for screening for a therapeutic drug for a disease of cerebral cortex or a surgical injury of cerebral cortex. This is specifically exemplified by the following methods (A) and (B).

(A) A method for screening for a therapeutic drug for a disease of cerebral cortex or a surgical injury of cerebral cortex, comprising the steps of contacting a test substance with a ubiquitin ligase complex containing CRBN and measuring a ubiquitin ligase activity of the ubiquitin ligase complex to select a test substance with an increased ubiquitin ligase activity.

(B) A method for screening for a therapeutic drug for a disease of cerebral cortex or a surgical injury of cerebral cortex, comprising the steps of culturing a neural stem cell or a neural progenitor cell in the presence of a test substance and measuring an expression level of CRBN in the neural stem cell or the neural progenitor cell to select a test substance with an increased expression level of CRBN.

In the method (A), the ubiquitin ligase activity can be measured in accordance with, for example, the method of Angers et al. (Nature, 443, 590-593, 2006) and the method of Groisman et al. (Cell, 113, 357-367, 2003).

In the method (A), whether or not the test substance has increased the ubiquitin ligase activity can be judged by measuring the ubiquitin ligase activity of a ubiquitin ligase complex containing CRBN without contacting with the test substance and making a comparison with the value thus obtained.

The substance thus selected by the method (A) acts to increase the ubiquitin ligase activity of the CRBN-containing ubiquitin ligase complex present in neural stem cells or neural progenitor cells in the living body. It is speculated that proliferation of neural stem cells or neural progenitor cells and differentiation of these cells into nerve cells effected by CRBN are mediated by the ubiquitin ligase activity possessed by this complex. Accordingly, it is assumed that the substance that is selected by the method (A) facilitates proliferation of neural stem cells or neural progenitor cells and differentiation of these cells into nerve cells effected by CRBN, and thus is therapeutically effective for a disease of cerebral cortex and a surgical injury of cerebral cortex.

In the method (B), as the neural stem cells to be used, basically cells such as ES cells, iPS cells, and adult stem cells that are subjected to neuronal differentiation induction are employed. Further, neural stem cells such as ones derived from the subventricular zone of adult mice or the hippocampus of adult rats may also be used.

In the method (B), a method for measuring the expression level of CRBN can be carried out by, for example, a method using an antibody against CRBN, in situ hybridization method, the RT-PCR method, and Northern blotting method.

In the method (B), whether or not the test substance has increased the expression level of CRBN can be judged by culturing neural stem cells or neural progenitor cells in the absence of the test substance and measuring the expression level of CRBN, and then making a comparison with the value thus obtained.

The substance that is selected by the method (B) acts to increase the expression level of CRBN in neural stem cells or neural progenitor cells in the living body. Accordingly, it is assumed that the substance that is selected by the method (B) facilitates proliferation of neural stem cells or neural progenitor cells and differentiation of these cells into nerve cells effected by CRBN, and thus is therapeutically effective for a disease of cerebral cortex and a surgical injury of cerebral cortex,

EXAMPLES

Hereinbelow, the present invention will be described in more detail with reference to Examples.

Experimental Methods (1) Systemic Gene Overexpression in the Zebrafish Embryo

Adult fish were reared at a constant temperature of 28.5° C. and maintained and bred under a diurnal cycle of 14 hours of light-on and 10 hours of light-off. Fertilized eggs were secured by natural mating between males and females, and an aqueous solution of 600 ng/µl capped RNA synthesized in vitro was injected into the cytoplasm of the embryos before the first cleavage (1-cell stage) under conditions of a nitrogen gas pressure of 30 psi and a valve opening time of 30 msec (millisecond). Because the expression of all the genes except the lhx2 gene (i.e., the crbn gene, the six3.2 gene, and a gene encoding a protein composing an E3 ubiquitin ligase complex with crbn) has little impact on the embryonic development, even when systemically expressed, this method was used to obtain the first data.

(2) Localized Gene Overexpression in the Head of the Zebrafish Embryo

For studying the lhx2 gene, which exhibits non-specific dorsalization of the embryo when systemically expressed, and for precise experiments specifically examining the effect exerted on the brain volume, in vivo RNA lipofection into the prospective head region of the embryo was carried out. The method of lipofection was entirely in accordance with the technique developed and published by Ando et al. (Ando and Okamoto, Efficient transfection strategy for the spatiotemporal control of gene expression in zebrafish. Mar. Biotechnol. 8(3): 295-303, 2006).

(3) Gene Knockdown Using the Zebrafish Embryo

An aqueous solution of a 25-mer antisense morpholino oligonucleotide (AMO, Gene Tools, LLC) corresponding to the vicinity of the translation initiation codon in the cDNA sequence of the gene to be knocked down (700 ng/µl, injection conditions were the same as those used for RNA) was injected into the embryos at the 1-cell stage. The sequence of AMO used for crbn gene knockdown is 5' AGAGCTGTAGCTGGTTCCCCATTTC 3' (SEQ ID NO:1), and that used for lhx2 gene knockdown is 5' TCTGCAACCCAAGATTTCCGTGAGA 3' (SEQ ID NO:2).

(4) Determination of Functional Hierarchy of Genes Using Zebrafish

This process was carried out entirely in accordance with the technique of Ando et al. (H. Ando et al., Lhx2 mediates the activity of Six3 in zebrafish forebrain growth. Dev. Biol. 287(2): 456-468, 2005) except for the following procedure. Head-specific gene expression was performed by the in vivo lipofection method described in (2) above instead of RNA uncaging (Japanese Patent Laid-Open No. 2002-315576, H. Ando et al., Photo-mediated gene activation using caged RNA/DNA in zebrafish embryos. Nat. Genet. 28, 317-325, 2001). The basic principle is as follows: embryos in which one (A) of the two kinds of genes suggested to have a functional association is knocked down by the method described in (3) above are cultured up to six hours after fertilization (gastrula stage), and in the prospective forebrain region of the embryos, the expression of the other gene (B) is induced by the in vivo lipofection method described in (2) above. When the effect of knocking down of A is rescued, whereas the effect of knocking down of B is not rescued by an inverted combination of A and B, within a 24-hour period after fertilization, it is determined that A lies functionally upstream of B.

(5) Immunohistochemistry

Antibody staining of early neurons of zebrafish was performed by the following technique. The embryos 24 to 28 hours after fertilization were fixed at 4° C. for 12 hours in a 4% paraformaldehyde/phosphate buffer (pH 8.0). After washing four times with phosphate buffer, where each wash was performed for 15 minutes, blocking was carried out at normal temperature for one hour in a 5% newborn goat serum dissolved in 0.5% Triton X-100/phosphate buffer. Primary antibody reaction was carried out using a monoclonal anti-acetylated tubulin antibody diluted at 1:1000 in the same solution at 4° C. for 12 hours. Then, after washing the embryos similarly with phosphate buffer, secondary antibody reaction was carried out using an anti-mouse antibody conjugated with Alexa Fluoro 488 (Molecular Probes) under the same conditions as those applied in the primary antibody reaction. The embryos were then washed with phosphate buffer and transparentized in 30%/50%/70% glycerol (dissolved in phosphate buffer), and then observed with a fluorescent microscope under excitation at 488 nm.

(6) Whole-Mount In Situ Hybridization

This process was carried out basically in accordance with the technique of Thisse et al. (Nat. Protocol. 3 (1) 59-69, 2008). The differences are that a 5 mg/ml Torula yeast RNA was used as a blocker in the probe hybridization solution and a 0.5% Blocking Reagent (Roche) was used as a blocker in the antibody reaction solution. The cDNA of the genes used as the probe (the six3.2 gene, the emx1 gene, the pax2.1 gene, the foxg1 gene, and the otx2 gene) are presents of the original provider. As the probe for the lhx2 gene, the one initially cloned by Ando was used. For the probes of the crbn gene and related genes, primers were designed based on the EST database of zebrafish and the probes were cloned from a cDNA library.

(7) Cell Transplantation

Nuclease-free water in which an appropriate concentration of rhodamine dextran (molecular weight 10,000) and a final centration of 600 ng/μl crbn RNA were dissolved was injected into the zebrafish embryos at the 1-cell stage under the conditions of the method described in (1) above, and the resulting embryos served as the donors. At three to four hours after fertilization of the donors, 10 to 50 cells were suctioned by a glass microcapillary under fluorescent microscopic observation, which were transplanted into the animal pole of the host embryos at the same stage. After culturing the host embryos for two days without adding any modification, localization of differentiation of the CRBN-expressing donor-derived cells was observed under a fluorescent microscope. Also, as a negative control, cells in which green fluorescence protein (GFP), which was assumed to have no effect on the embryonic development, was expressed were transplanted under the same conditions, and localization of the differentiation was compared between the experimental and control embryos.

(8) Detection and Measurement of the Ubiquitin Ligase Activity of CRBN Using an In Vitro Reaction System This process was carried out basically in accordance with the method of Groisman et al. Firstly, CRBN and a binding protein (referred to as a CRBN complex) were purified from a cell lysate solution of mammalian cells expressing CRBN fused with a FLAG epitope tag using M2 FLAG agarose beads (SIGMA). Subsequently, the CRBN complex thus purified was mixed with an aqueous solution containing Uba1 (E1), UbcH5b (E2), and a recombinant GST fusion ubiquitin (Ub) protein, and after addition of ATP, the mixture was left to stand at 30 to 37° C. for two hours. Thereafter, the reaction was terminated by SDS, and self-ubiquitination and ubiquitination of the binding protein were visualized by polyacrylamide gel electrophoresis and immunoblotting, whereby the ubiquitin ligase activity was detected and measured.

(9) Detection and Measurement of the CRBN Ubiquitin Ligase Activity Using Live Cells This process was carried out basically in accordance with the method of Ohtake et al. MG132, which is a proteasome inhibitor, was applied to mammalian cells expressing CRBN fused with a FLAG epitope tag, and the cells were left still. Subsequently, the cells were disrupted, and from the resulting cell lysate solution, FLAG was purified and CRBN was extracted, and then immunoblotting was performed under similar, but stricter, conditions to the above, whereby the self-ubiquitination was detected and measured.

(10) Fluorescent Staining of Glia Cells and Serotonin-Producing Cells

Two-day-old zebrafish were used (for glia cell staining and serotonin-producing cell staining, zebrafish 56 hours and 49 hours after fertilization were used, respectively). Zebrafish were fixed with 4% paraformaldehyde (PFA) and then washed with phosphate buffer (PBS), followed by treatment with 10 μg/ml protease K for partial digestion of the epidermis. After the digestion reaction, the zebrafish were washed with PBST (PBS+0.5% Triton X-100) for 20 minutes and then fixed with PFA again. The fixed zebrafish were washed with PBST at room temperature for one hour, followed by blocking using PBST+5% goat serum. The resulting specimens were reacted with a monoclonal anti-glia antibody (zrf-1/zrf-2) or a rabbit anti-serotonin antibody at 4° C. overnight (12 to 18 hours). Subsequently, the specimens were washed with PBST+5% goat serum for one hour at room temperature, and secondary antibody reaction was carried out by substituting the antibody for a goat anti-mouse IgG antibody (Cy-2 conjugate for glia cell staining) or a goat anti-rabbit IgG antibody (Cy-5 conjugate for serotonin-producing cell staining) at 4° C. overnight (12 to 18 hours). Subsequently, the specimens were washed with PBST at room temperature for one hour. After washing, PBST was replaced by 30%, 50%, 70% glycerol/PBS and the whole zebrafish were mounted on glass slides to obtain preparations. Fluorescence was observed under excitation wavelength of Cy-2 and Cy-5 and the distribution of the glia cells or the serotonin-producing cells was recorded. It is to be noted that glia cells were observed from the lateral side of zebrafish, while the serotonin-producing cells were photographed from the dorsal side in order to observe the distribution of the cells along the midline.

(11) Transplantation of CRBN-Expressing Cells into the Diencephalic Ventricle

A mixed solution of CRBN-coding RNA (700 ng/μl) and 2% rhodamine dextran was injected into the zebrafish embryos at the 1-cell stage immediately after fertilization. The embryos were cultured up to four hours after fertilization and 10 to 20 cells were collected by a suction capillary, which were injected into the diencephalic ventricle of embryos 30 hours after fertilization, whereby the cells were transplanted. Zebrafish having undergone transplantation were reared up to three days after fertilization in zebrafish physiological saline (E3 Ringer) and then fixed with 4% paraformaldehyde. Following the ordinary method, primary antibody reaction and secondary antibody reaction were carried out using a monoclonal anti-acetylated tubulin antibody and an anti-mouse IgG antibody conjugated with Alexa Fluor® (excited at 488 nm), respectively. Then, while observing the fluorescently-labeled nerve cell axon, distribution of the transplanted cells labeled with rhodamine dextran (excited at 543 nm) was studied.

Experimental Results (1) Determination of Functional Hierarchy of Lhx2 and CRBN

Compared to the normal embryo (FIG. 1, upper left panel), brain shrinkage was observed in the lhx2 gene-knockdown embryo (FIG. 1, lower left panel). Meanwhile, similarly to the crbn gene-overexpressing embryo (FIG. 1, upper right panel), brain enlargement was observed in the embryo in which lhx2 gene was knocked down while crbn gene was overexpressed (FIG. 1, lower right panel). From this observation, it is considered that CRBN functions downstream of Lhx2, directly inducing proliferation of central nervous stem cells and differentiation of these cells into nerve cells.

(2) CRBN Overexpression Experiment

Figure 2:
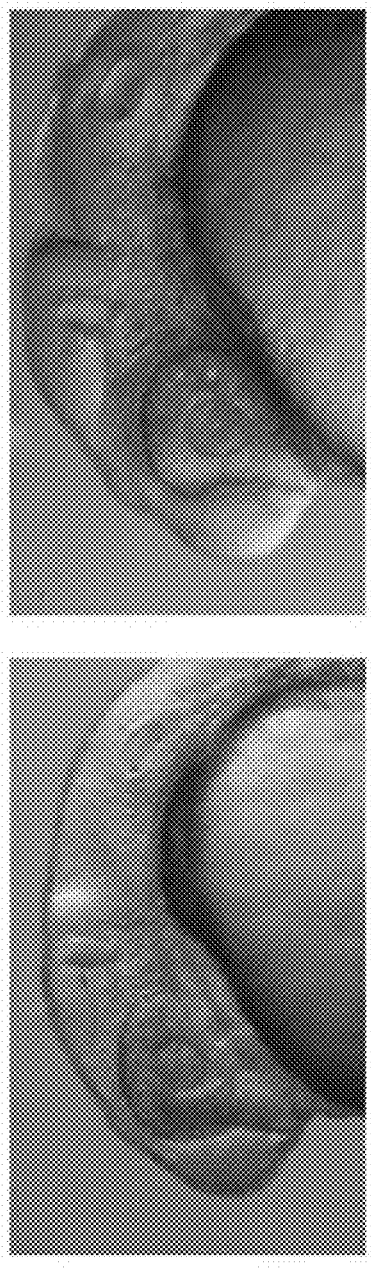
FIG. 2 shows microscopic pictures of zebrafish embryos. The picture on the right shows an embryo in which the crbn gene is overexpressed and the picture on the left shows an untreated embryo. Both pictures were taken at the same magnification.

In order to verify induction of differentiation into neural stem cells by CRBN in the cerebrum, a CRBN overexpression experiment was carried out in the forebrain and midbrain of the zebrafish embryos. As a result, both brains enlarged approximately 1.5 times in volume, while retaining their shape (FIG. 2, right). Moreover, the neuron network in the brain was morphologically normal (FIG. 2, right).

(3) Transplantation Experiment of CRBN-Overexpressing Cells

Figure 3:
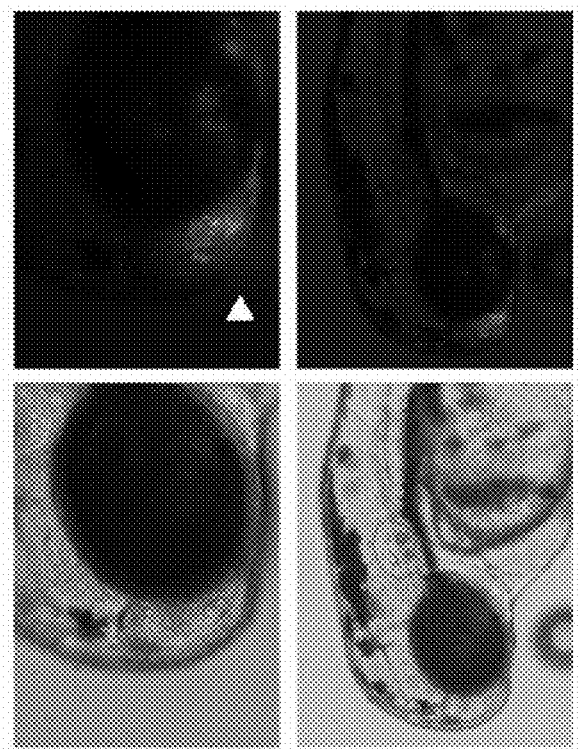
FIG. 3 shows microscopic pictures of zebrafish, into which crbn gene-overexpressing cells (fluorescently labeled with rhodamine) are transplanted. The top pictures and the bottom pictures were taken at 200-fold magnification and 100-fold magnification, respectively. Also, the pictures on the left column are bright-field images and the pictures on the right column are fluorescent images.

Firstly, mRNA encoding CRBN and a fluorescent substance (rhodamine) were injected together into donor embryos so that CRBN was overexpressed. The resulting blastula was transplanted into another individual and differentiation of donor-derived cells distributed in the cerebral ventricle was observed under a fluorescent microscope. As a result, the transplanted donor-derived cells were significantly differentiated into the olfactory bulb, which is the telencephalon tissue of fish (FIG. 3, arrowhead). This indicates that when the CRBN-expressing cells were distributed into the cerebral ventricle, they differentiated into neural stem cells and migrated along a cell migration pathway called Rostral Migratory Stream (RMS) and differentiated into the brain tissue in the dorsal telencephalon, where the cerebral cortex develops in mammals.

Figure 4:
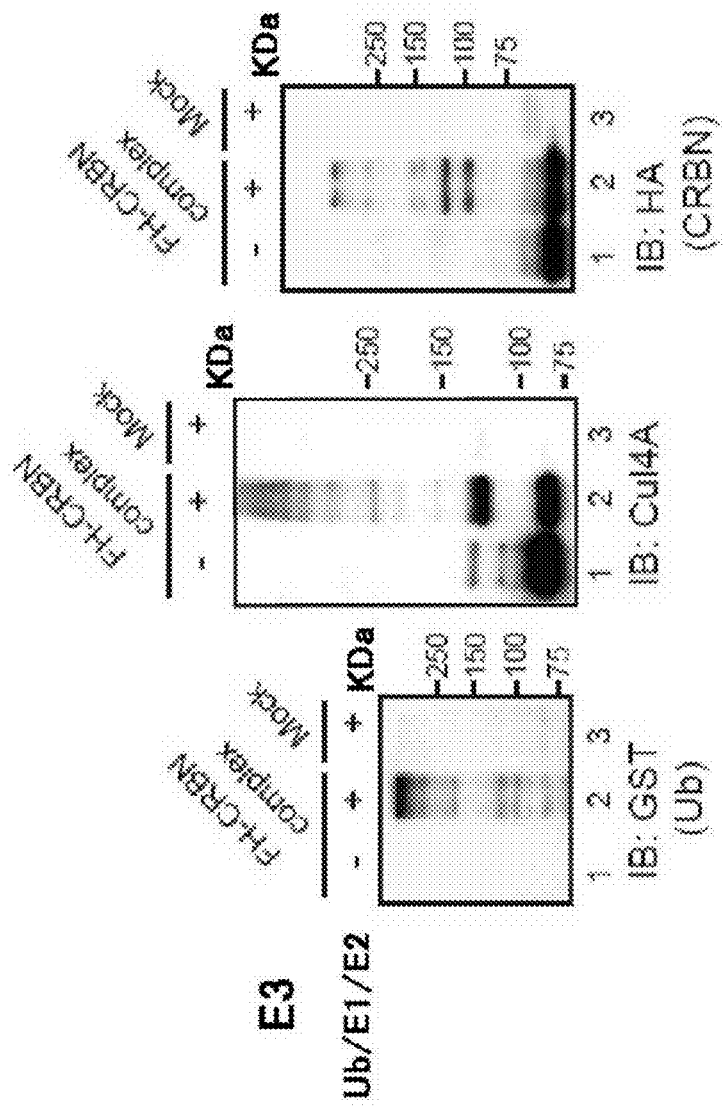
FIG. 4 shows electrophoresis images for the detection of the ubiquitin ligase activity of a CRBN complex (FH-CRBN complex) using an in vitro reaction system. The images on the left, middle, and right show ubiquitin, Cul4A, which is a CRBN complex-forming factor, and ubiquitinated CRBN, respectively, each detected by immunoblotting. Mock indicates the case of the use of a control experimental sample.

(4) Detection and Measurement of the Ubiquitin Ligase Activity of CRBN Using an In Vitro Reaction System When CRBN (FH-CRBN complex) was added to an aqueous solution containing Uba1 (ubiquitin activating enzyme), UbcH5b (ubiquitin transfer enzyme), and a recombinant GST fusion ubiquitin protein (Ub/E1/E2), proteins that would not be detected in the absence of addition of CRBN were detected (FIG. 4, lane 2 in the left, middle, and right images). For ubiquitination of a protein, in addition to ubiquitin, three kinds of enzymes, namely a ubiquitin activating enzyme, a ubiquitin transfer enzyme, and a ubiquitin ligase are needed. Ubiquitinated proteins were not existent in lane 1 of the left, middle, and right images because no ubiquitin ligase was present. Meanwhile, in lane 2 of the left, middle, and right images, it is speculated that CRBN acted as a ubiquitin ligase to produce ubiquitinated proteins, which were detected by electrophoresis.

Figure 5:
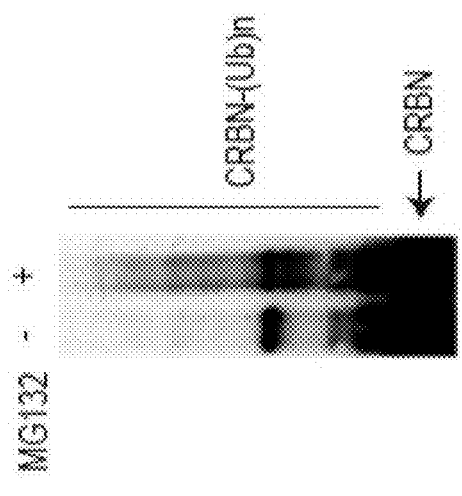
FIG. 5 shows an electrophoresis image for the detection of the ubiquitin ligase activity of the CRBN complex in live cells.

(5) Detection and Measurement of the CRBN Ubiquitin Ligase Activity Using Live Cells When MG132 was added, a number of bands representing the CRBN-containing proteins were detected (FIG. 5, the right lane). In contrast, when MG132 was not added, very few bands representing the CRBN-containing proteins were detected (FIG. 5, the left lane).

It is considered that CRBN in live cells undergoes self-ubiquitination in cooperation with other factors and yields ubiquitinated proteins of various molecular weights. However, most of them are assumed to be degraded by intracellular proteasome. In the left lane of FIG. 5, it is speculated that proteasome was inhibited by MG132, enabling proteins produced through self-ubiquitination to remain, leading to detection of a number of bands. In contrast, in the right lane of FIG. 5, it is speculated that very few bands were detected because most of the proteins produced were degraded by proteasome.

(6) Fluorescent Staining of Glia Cells and Serotonin-Producing Cells

Figure 6:
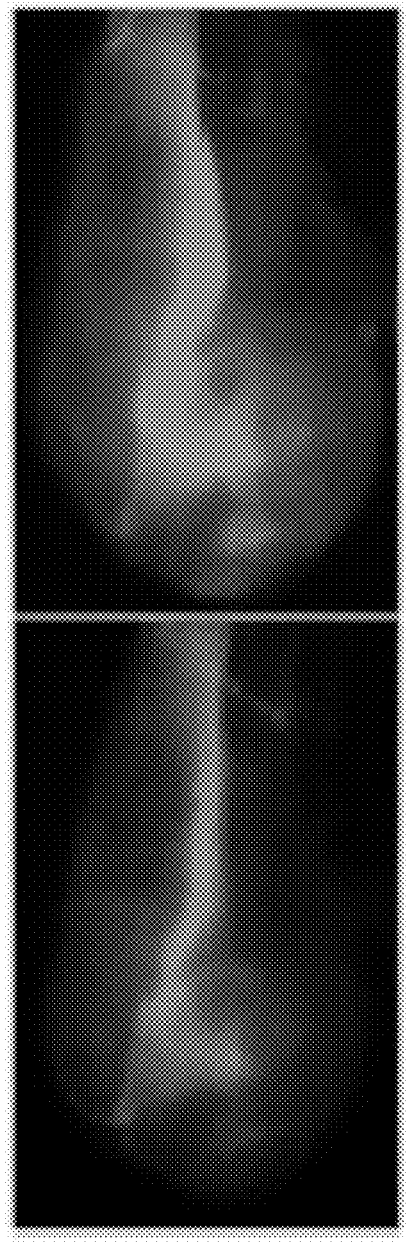
FIG. 6 shows close-up pictures of zebrafish heads in which glia cells were fluorescently stained. The left part of the picture corresponds to the front end portion. The picture on the left shows a normal individual and the picture on the right shows an individual with overexpressed CRBN.
Figure 7:
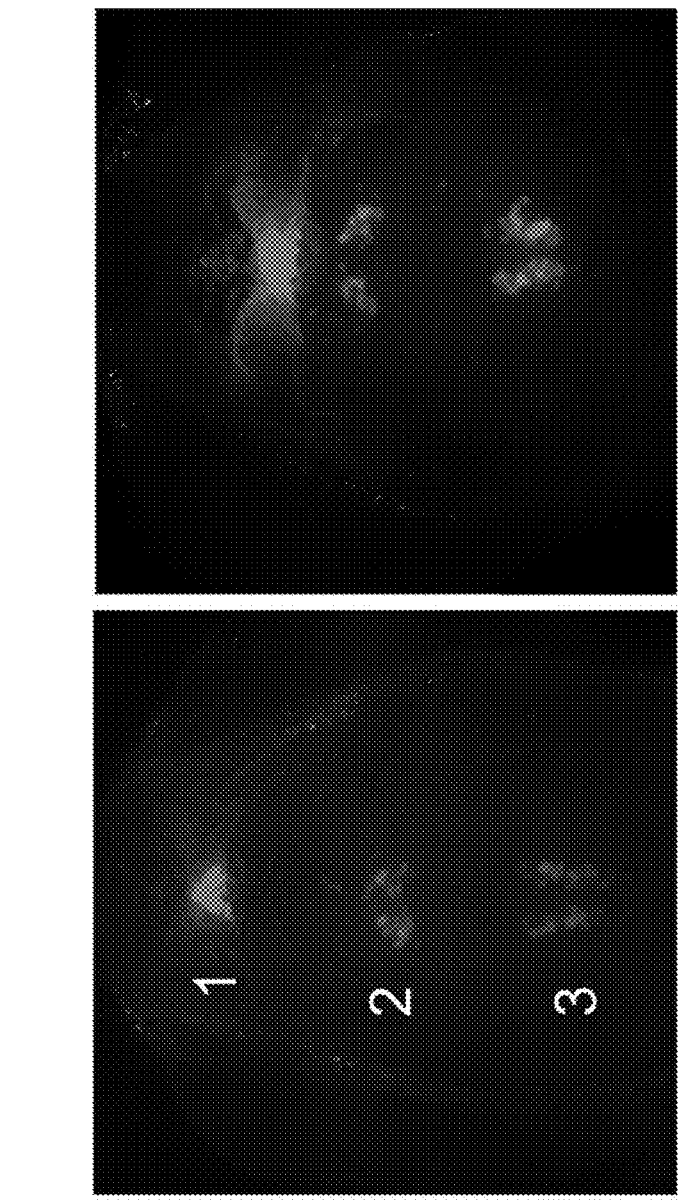
FIG. 7 shows close-up pictures of zebrafish heads in which serotonin-producing cells were fluorescently stained. These pictures were taken from the dorsal side of the brain. The top part of the picture corresponds to the front end portion. The picture on the left shows a normal individual and the picture on the right shows an individual with overexpressed CRBN. In the figure, numbers 1, 2, and 3 indicates the pineal gland, the ventral posterior tuberculum, and the raphe nucleus, respectively.

In the CRBN-overexpressing individual, glia cells (FIG. 6, the left picture) and serotonin-producing cells (FIG. 7, the left picture) were increased, while normal spatial distribution was maintained. This means that CRBN acts to proliferate and differentiate cells, while normally recognizing the spatial pattern of the brain.

(7) Transplantation of CRBN-Expressing Cells into the Diencephalic Ventricle

Figure 8:
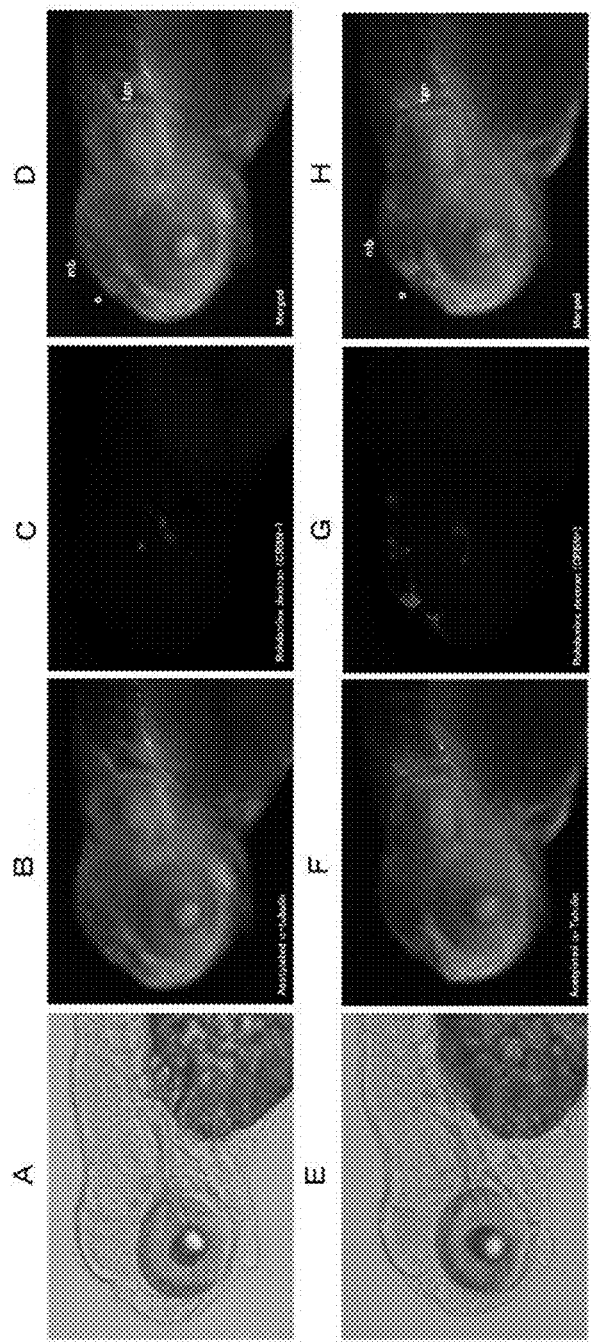
FIG. 8 shows pictures of zebrafish in which undifferentiated cells are transplanted into the cerebral ventricle. The upper panel (Parts A to D) of FIG. 8 show the cases in which cells that do not express CRBN are transplanted, and the lower panel (Parts E to H of FIG. 8) show the cases in which cells that express CRBN are transplanted. Parts A and E of FIG. 8 are bright-field images, Parts B and F of FIG. 8 are fluorescence images of Alexa Fluor® (indicating the distribution of tubulin), Parts C and G of FIG. 8 are fluorescence images of rhodamine (indicating the distribution of donor cells), and Parts D and H of FIG. 8 are fluoresce images of Alexa Fluor® and rhodamine.

When the cells that do not express CRBN were transplanted, the cells did not differentiate into the brain tissue (the upper panel (Parts A to D) of FIG. 8), whereas when the cells that express CRBN were transplanted, the cells differentiated into the brain tissue (the lower panel (Parts E to H) of FIG. 8).

SEQUENCE LISTING

The present specification is being filed with a computer readable form (CRF) copy of the Sequence Listing. The CRF entitled 12827-710-999_SEQLIST.txt, which was created on Jan. 30, 2015 and is 983 bytes in size, is identical to the paper copy of the Sequence Listing and is incorporated herein by reference in its entirety.

The invention claimed is:

1. A method for screening for a therapeutic drug for a disease of cerebral cortex or a surgical injury of cerebral cortex, comprising:
   contacting a test substance with a ubiquitin ligase complex comprising cereblon (CRBN);
   measuring a ubiquitin ligase activity of the ubiquitin ligase complex;
   selecting the test substance that increased the ubiquitin ligase activity of the ubiquitin ligase complex as compared with a ubiquitin ligase activity of the ubiquitin ligase complex without contacting the test substance; and
   identifying the substance as a potential therapeutic drug for a disease of cerebral cortex or a surgical injury of cerebral cortex.

2. The method of claim 1, wherein the disease of cerebral cortex is selected from the group consisting of Alzheimer's disease, Parkinson's disease, Creutzfeldt-Jakob disease, Huntington's disease, progressive supranuclear palsy, and corticobasal degeneration.

3. The method of claim 1, wherein the ubiquitin ligase complex comprising CRBN is from a neural stem cell or a neural progenitor cell of a subject.

* * * * *

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: sequence of AMO used for crbn gene knockdown

<400> SEQUENCE: 1
```

```
agagctgtag ctggttcccc atttc                                         25

<210> SEQ ID NO 2
<211> LENGTH: 25
<212> TYPE: DNA
<213> ORGANISM: Artificial Sequence
<220> FEATURE:
<223> OTHER INFORMATION: sequence of AMO used for lhx2 gene knockdown

<400> SEQUENCE: 2
tctgcaaccc aagatttccg tgaga                                         25
```